Figure 1:
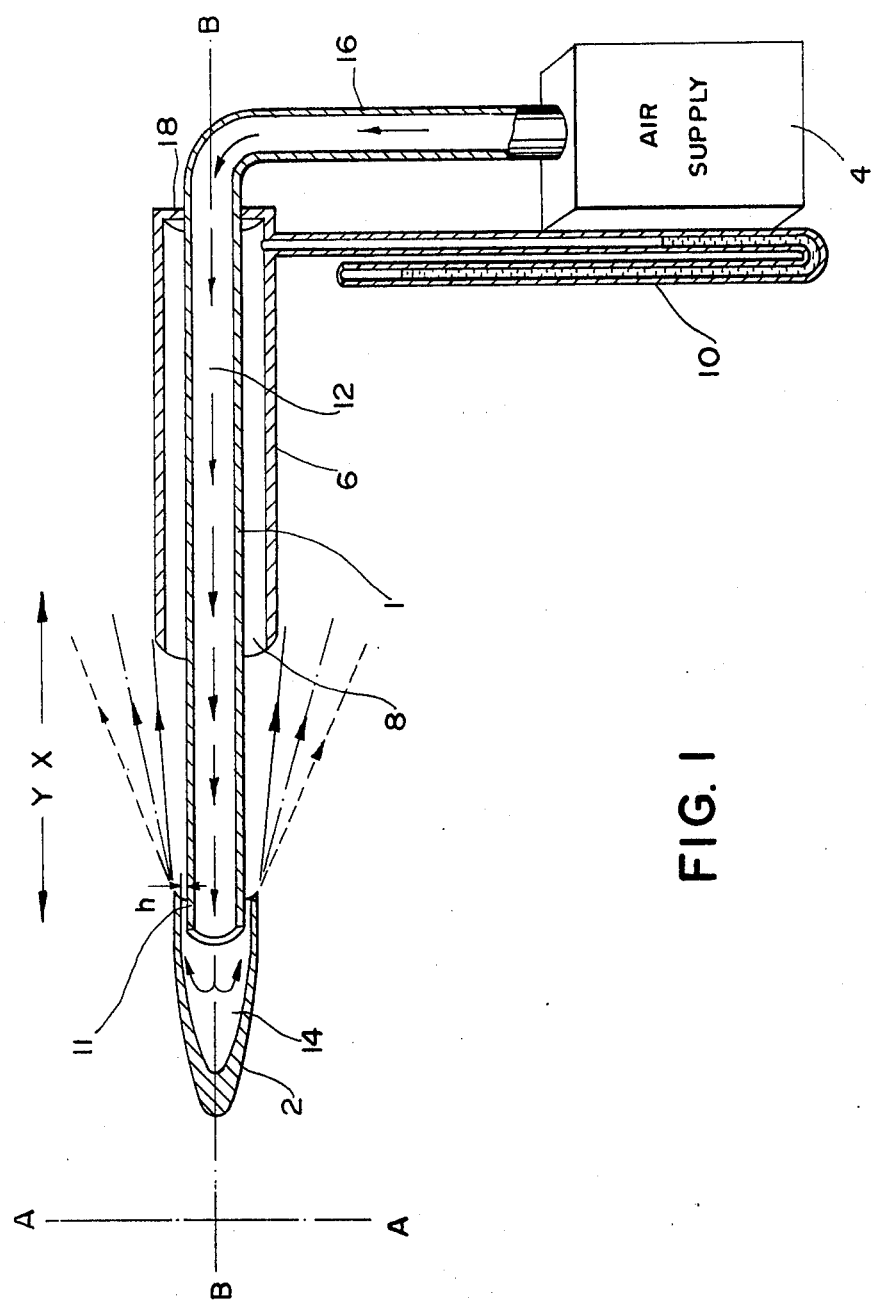

United States Patent [19]

Tanney

[11] 3,969,938

[45] July 20, 1976

[54] APPARATUS FOR MEASURING THE VELOCITY AND/OR DENSITY OF A FLUID STREAM

[75] Inventor: John W. Tanney, Ottawa, Canada

[73] Assignee: Canadian Patents and Development Limited, Ottawa, Canada

[22] Filed: Feb. 18, 1975

[21] Appl. No.: 550,560

[30] Foreign Application Priority Data

May 13, 1974 Canada................................. 199720

[52] U.S. Cl.................................. 73/189; 73/194 R
[51] Int. Cl.² ......................... G01N 9/32; G01F 1/00
[58] Field of Search............. 73/194 R, 205 R, 189, 73/32; 137/803, 804

[56] References Cited
UNITED STATES PATENTS

| | | | |
|---|---|---|---|
| 3,686,937 | 8/1972 | Corey ............................ | 73/194 X |
| 3,705,534 | 12/1972 | Turek .............................. | 73/194 |

OTHER PUBLICATIONS

"Fluidic Wind Sensor Aids Low Airspeed Measurement" in *Control Engineering*, Apr. 1971, vol. 18, No. 4, p. 41.

Primary Examiner—Herbert Goldstein
Attorney, Agent, or Firm—Francis W. Lemon

[57] ABSTRACT

A robust apparatus for measuring the velocity and/or density of a fluid stream comprises a cap-shaped nozzle which deflects pressurized fluid, issuing from a tube whose end is within the nozzle, back along the external surface of the tube to a receiver so that pressure indicated by a pressure measuring device attached to the receiver measures the velocity and/or density of a fluid stream flowing over the cap along the tube and over the receiver. The receiver may be an oversize, open ended receiver tube coaxial with receiver tube enclosing an annular receiver space around the tube. The receiver may also be a plurality of open ended receiver tubes around the tube, each attached to a different pressure measuring device so that a component of flow of and/or the density of a fluid stream transverse to the tube can be measured.

The nozzle orifice geometry is defined in relation to the Reynolds number at the nozzle orifice in order that the pressurized fluid issues from the nozzle orifice as turbulent flow and the fluid pressure in the receiver is related to the velocity and/or density of the fluid stream in a consistent manner in any number of tests.

5 Claims, 29 Drawing Figures

APPARATUS FOR MEASURING THE VELOCITY AND/OR DENSITY OF A FLUID STREAM

This invention relates to apparatus for measuring the velocity and/or density of a fluid stream.

There are many applications in which it is desirable to accurately measure the velocity and/or density of a fluid stream over a wide range of velocities and/or densities. Present devices such as hot wire and hot film gauges for measuring the velocities of fluid streams are delicate and require elaborate electronic equipment in their operation. Pitot tubes suffer from having outputs that are not proportional to the fluid stream velocity and their sensitivity is dependant on the sensitivity of their associated pressure measuring apparatus, which generally limits their usefulness to velocities of greater than 10 feet per second in air, except under specialized laboratory conditions. The use of rotating devices, for measuring the velocities of fluid streams, such as cup or propeller anemometers and their liquid counterparts provide an output proportional to the velocity of the measured stream but such instruments tend to stall at low velocities and their susceptibility to mechanical damage further limits their usefulness. Furthermore, such rotating devices, when designed to measure high fluid velocities, have limited usefulness at low velocities and when designed to measure low velocities they are generally of limited use and are subjected to damage at high velocities.

It is an object of the present invention to provide an apparatus for measuring the velocity of a fluid stream over a wider range of velocities than has been possible with the above mentioned devices, and to a greater accuracy than has been possible with such devices.

It is a further object of the invention to provide an apparatus for measuring the velocity of a fluid, which is robust in construction and is easily and economically manufactured.

More recently, it has been proposed to measure the velocity of a fluid stream by a device wherein a jet of fluid from a nozzle is directed towards the open end of at least one receiver tube. Changes in the fluid pressure in the or each receiver tube are measured to determine the velocity of a fluid stream flowing along the axis of the jet around the nozzle and receiver tube. If more than one receiver is used the direction of flow of the fluid stream can also be deduced. While this device is useful it would be advantageous to reduce the mixing of the jet with fluid stream, and so effect a reduction in the spreading angle of the jet, so that there would be an increase in the total head pressure on the receiver tube or tubes. This total head pressure would then be a function of the fluid supply pressure to the nozzle, the geometry of the nozzle and receiver and, if one receiver tube is used, the principle velocity component of the fluid stream along the axis of the jet. Thus the device would have a lower output noise level with consequent greater dynamic range and would be more rugged than similar devices in which the nozzle and/or receivers consist of simple tubes, particularly when a plurality of receiver tubes are used to measure the velocity of a fluid stream having a second velocity component transverse to the direction of flow of the jet.

It is an object of the present invention to provide an apparatus for measuring the velocity of a fluid stream wherein a jet of fluid from a nozzle is directed towards the open end of at least one receiver tube, and wherein a reduction is achieved in the mixing of the jet with the fluid stream, when compared with known devices, and thus a reduction is effected in the spreading angle of the jet so that the apparatus has a lower noise output when compared with known devices and is capable of measuring a wider range of velocities of fluid streams.

Turning now to apparatus for measuring the density of a fluid, that is, a fluid densitometer, it should ideally respond only to the density of the fluid to be measured and should have substantially no component of velocity with regard to the density measurement. In other respects a fluid densitometer should also be substantially insensitive to its environment. Ruggedness is also a very important feature for a fluid densitometer because then the probability of damage during installation and use is reduced.

Yet a further object of the present invention is to provide a fluid densitometer which is substantially insensitive to its environment and which is rugged.

According to the present invention there is provided an apparatus for measuring the velocity and/or density of a fluid stream comprising:

a. an elongated, fluid guiding member which is symmetrical in cross-section about at least one plane passing through and along a longitudinal axis of the elongated, fluid guiding member, with said longitudinal axis extending along a portion of the flow path of said fluid stream, b. nozzle means for directing pressurized fluid along and in contact with at least substantially identical opposing surface portions of said member on each side of said plane, c. means for supplying said nozzle means with said pressurized fluid, d. receiver means having at least one receiver mouth, in the path of said fluid from said nozzle means, to have fluid pressure imposed therein from said fluid directed along said opposing surface portions from said nozzle means, and, e. indicating means connected to said receiver means for indicating, in terms of the fluid pressure therein, the velocity and/or density of said fluid stream, and wherein, f. the nozzle means has a nozzle orifice whose geometry is such that the Reynolds number at the nozzle orifice is greater than 2,300 as defined in consistent units by:

$$Re = h\rho V/\mu$$

where
$Re$ = dimensionless Reynolds number
$h$ = the mean height of the nozzle orifice normal to the surface of the fluid guiding number
$\rho$ = the density of the pressurized fluid supplied to the nozzle means when the apparatus is in use,
$V$ = the mean velocity of the pressurized fluid in the nozzle orifice when the apparatus is in use, and
$\mu$ = the viscosity of the pressurized fluid in the nozzle orifice when the apparatus is in use.

Preferably the elongated, fluid guiding member is circular in cross-section.

The nozzle means preferably directs fluid along, and around the whole of, the elongated, fluid guiding member, and the receiver means preferably has a receiver mouth which is pressurized by fluid around the whole of the elongated, fluid guiding member.

In another preferred embodiment the nozzle means directs fluid along, and around the whole of the circular cross-section of, said elongated, fluid guiding member, and said receiver means has two receiver mouths on diametrically opposite sides of the elongated, fluid guiding member, and aligned with said opposing surface portions.

In yet another preferred embodiment the elongated, fluid guiding member has a fluid passage extending therealong to an open end thereof remote from the receiver means, the nozzle means is a hollow cap over the open end and is for redirecting fluid, flowing along the fluid passage, along the opposing surface portions, and the means for supplying the nozzle with pressurized fluid is connected to the elongated, fluid guiding member to supply pressurized fluid along the fluid passage towards the open end thereof.

Figure 2:
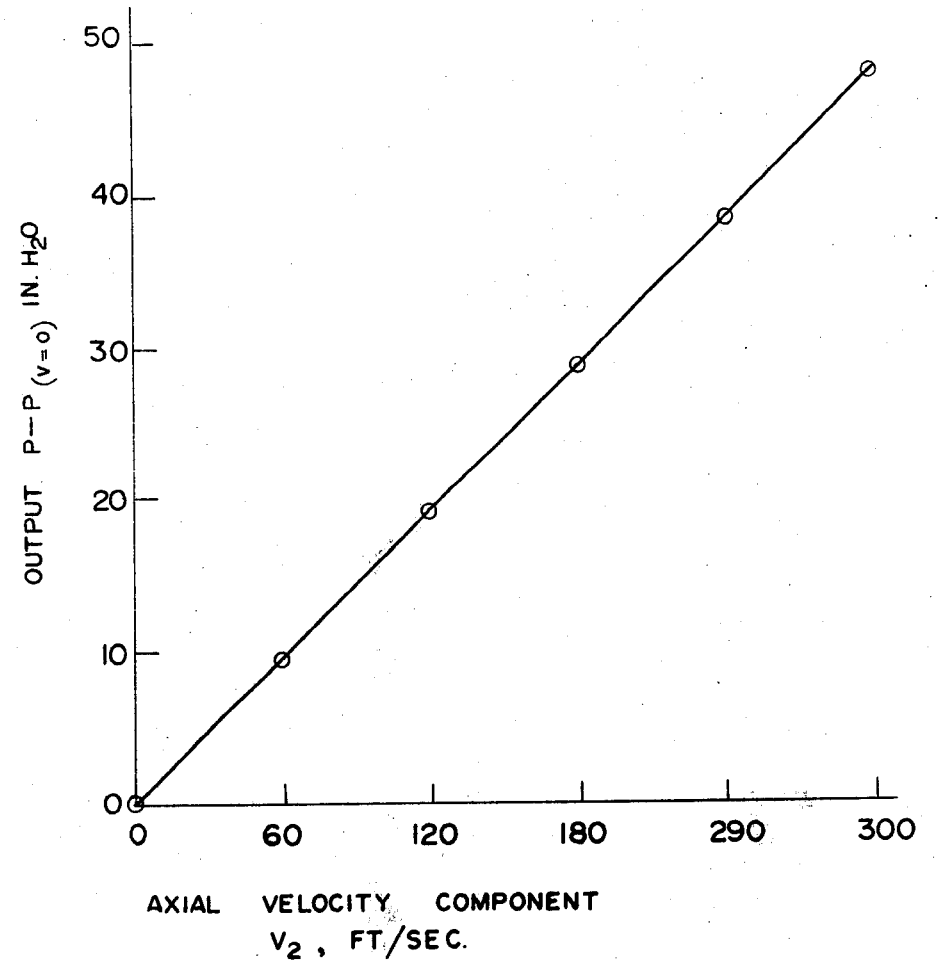
Figure 3:
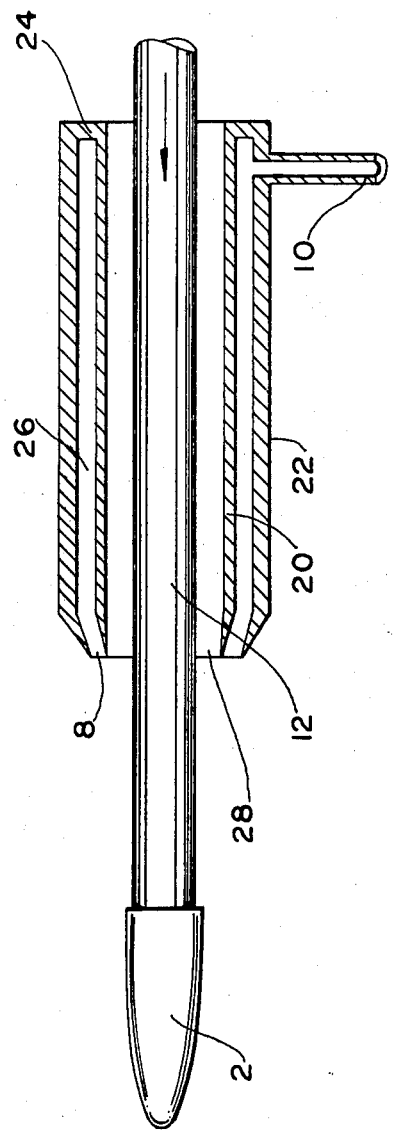
Figure 4:
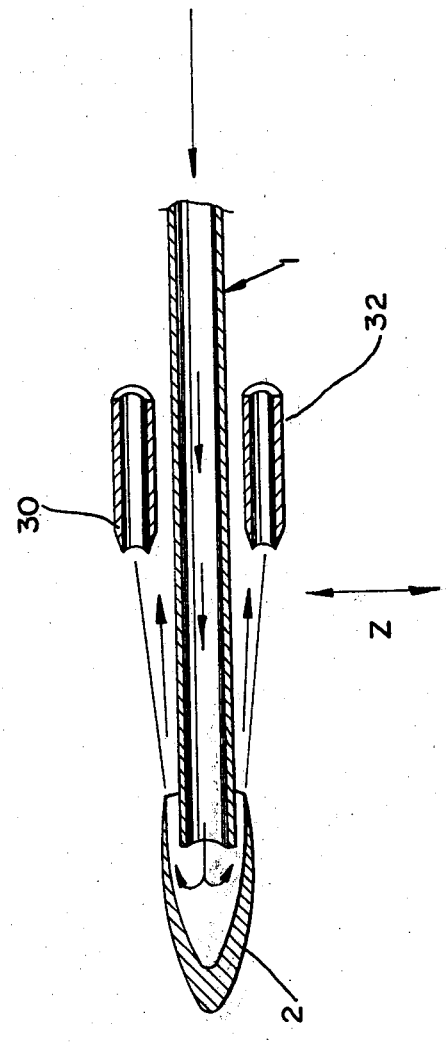
Figure 5:
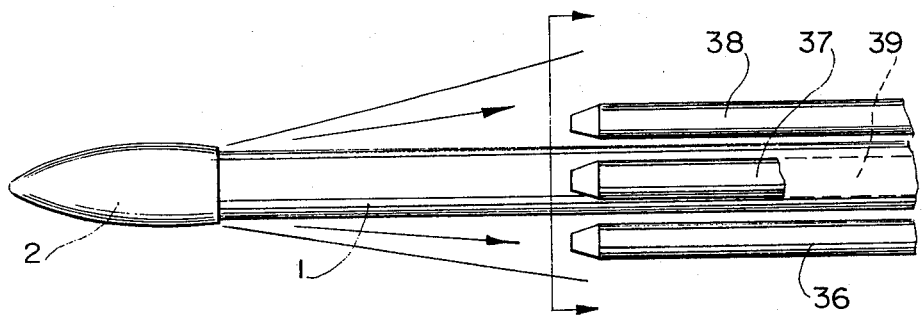
Figure 6:
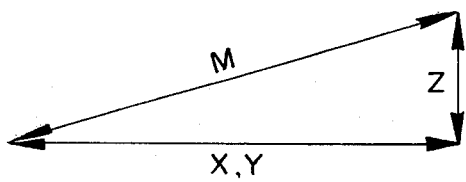
Figure 7:
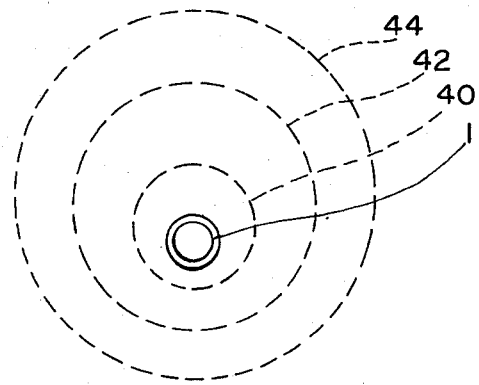
Figure 8:
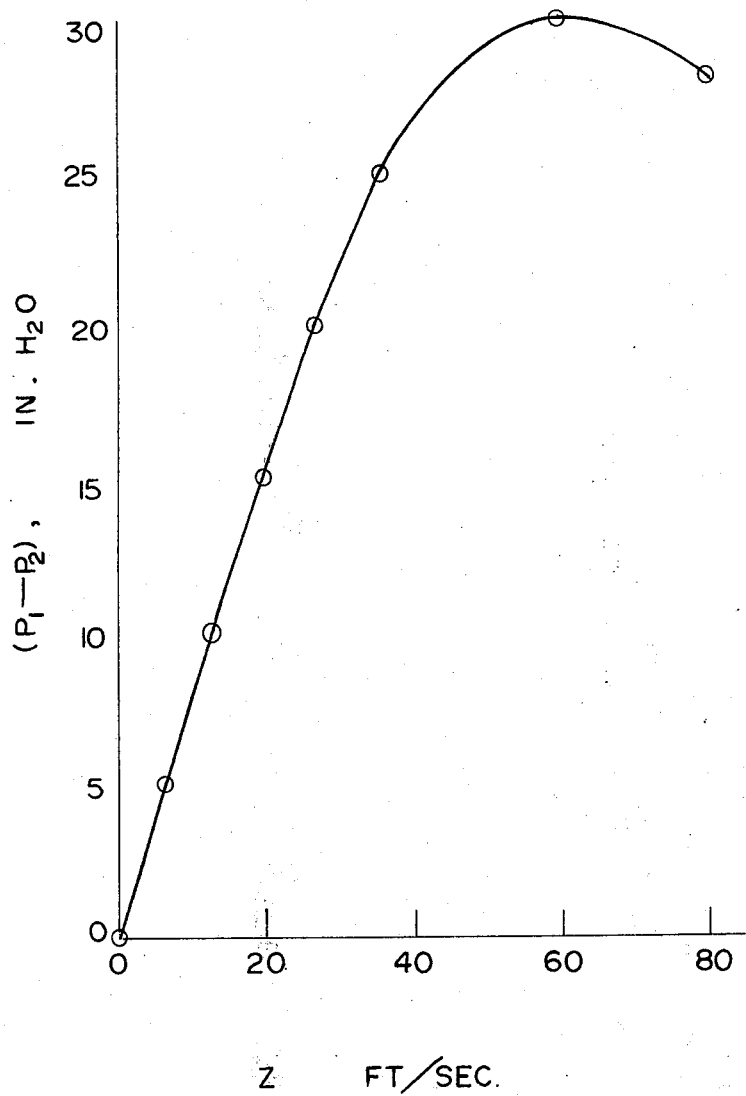
Figure 10:
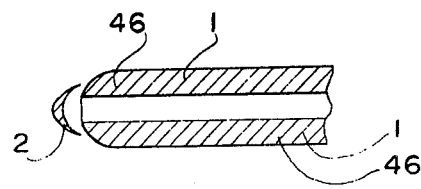
Figure 11:
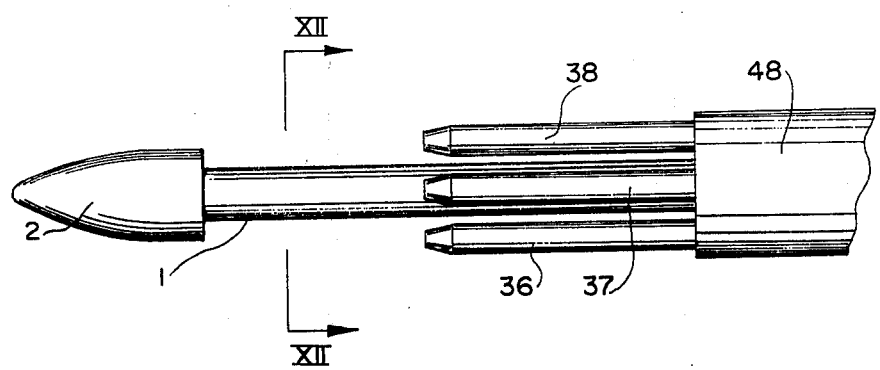
Figure 12:
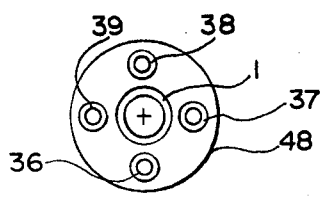
Figure 14:
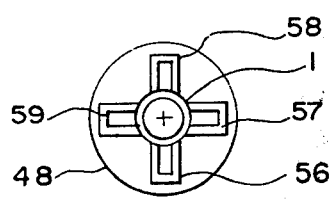
Figure 15:
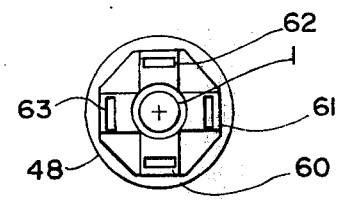
Figure 16:
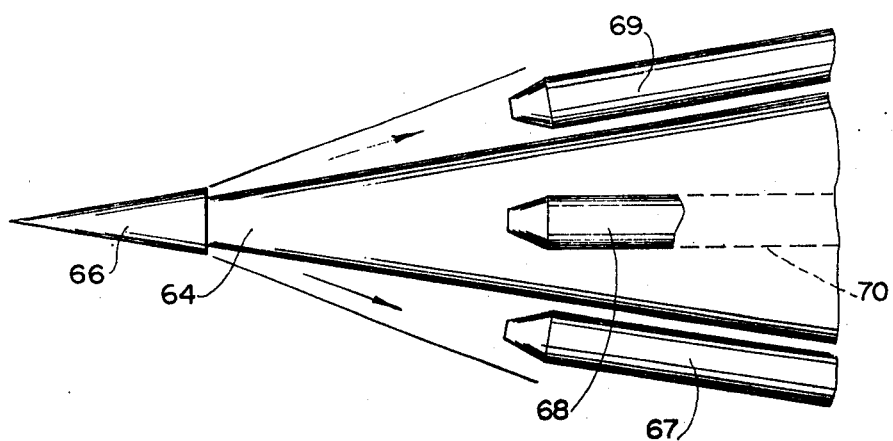
Figure 17:
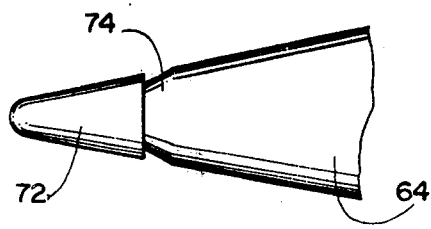
Figures 18, 19:
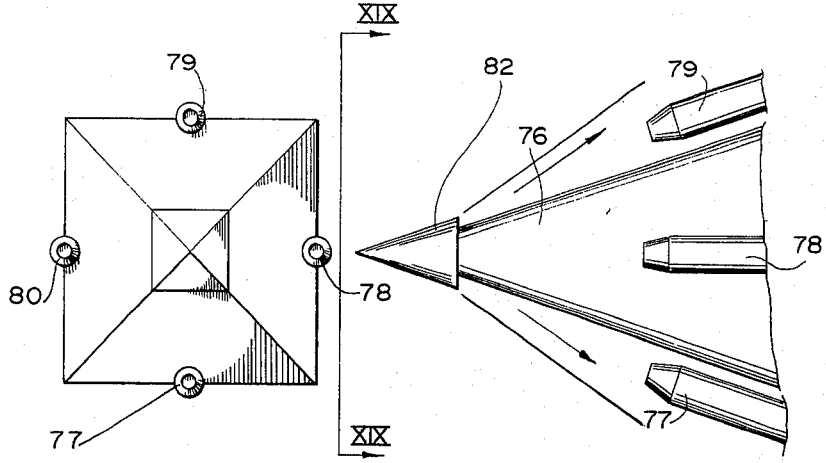
Figure 20:
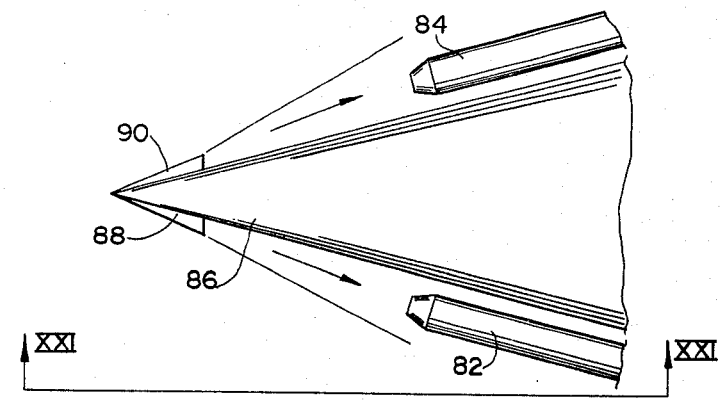
Figure 21:
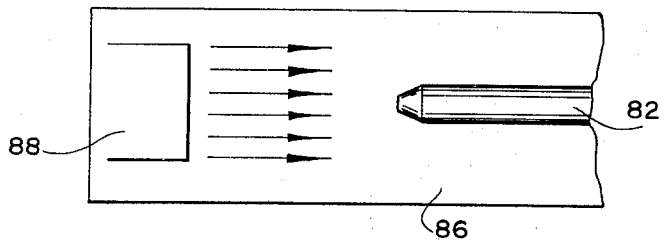
Figure 22:
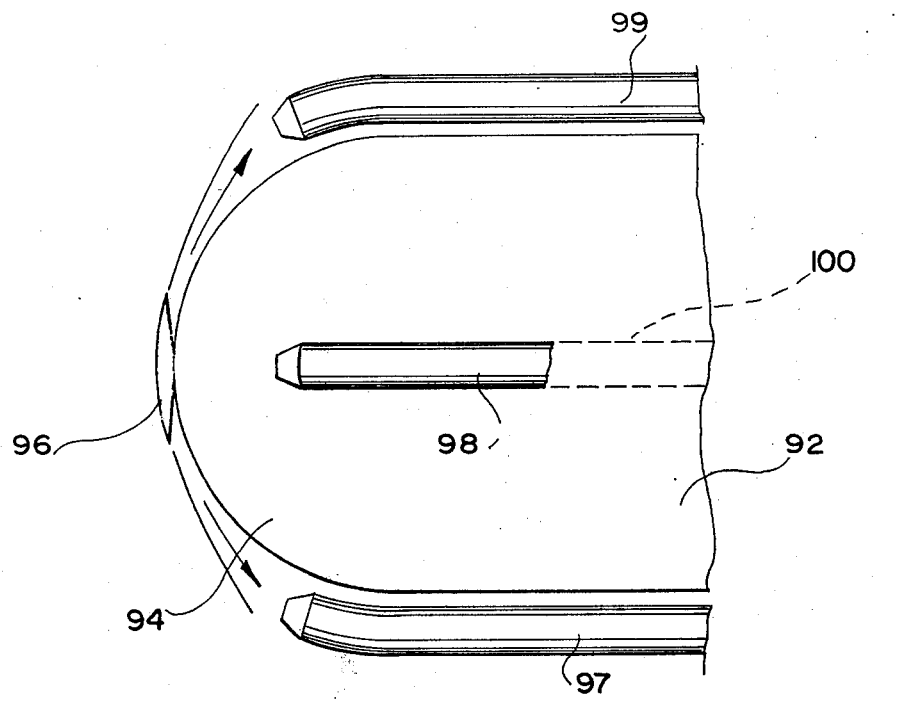
Figure 23:
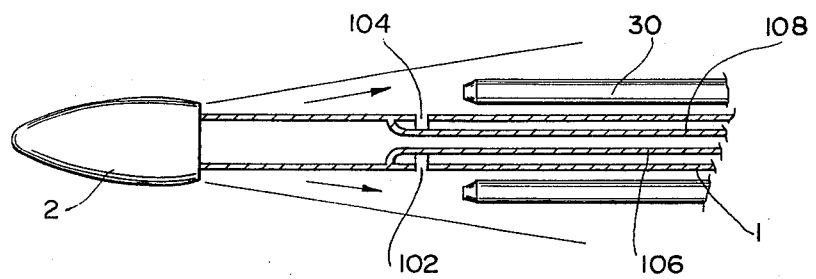
Figure 24:
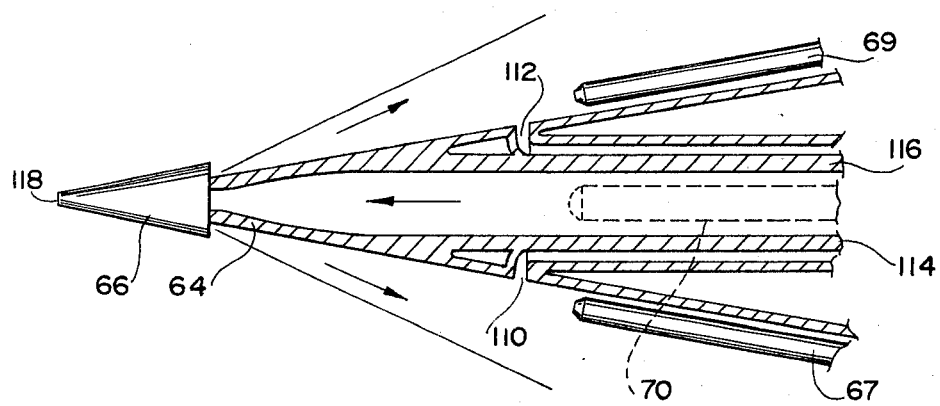
Figure 25:
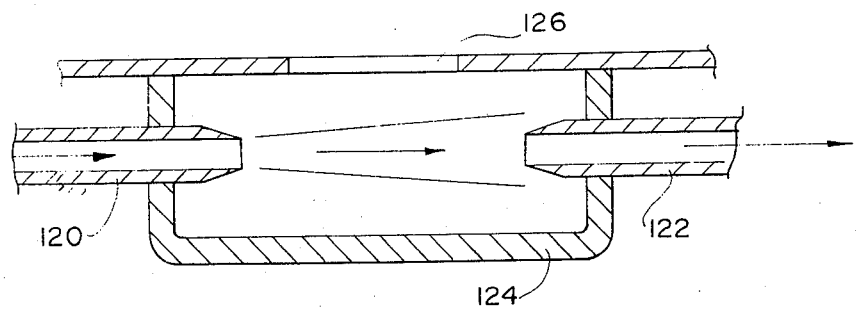
Figure 26:
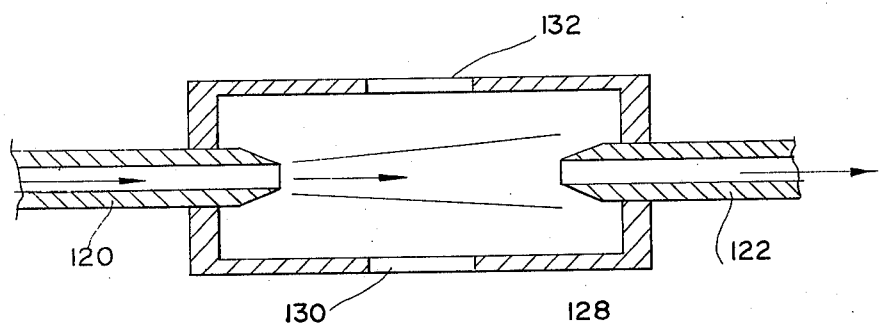
Figure 27:
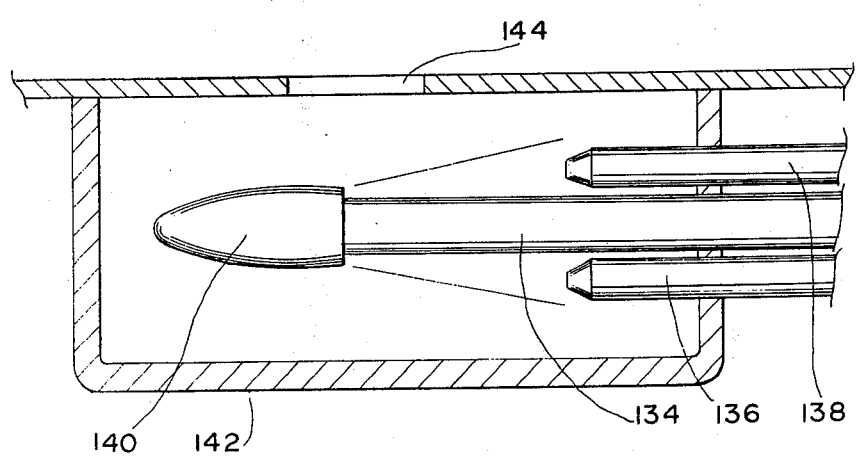
Figure 28:
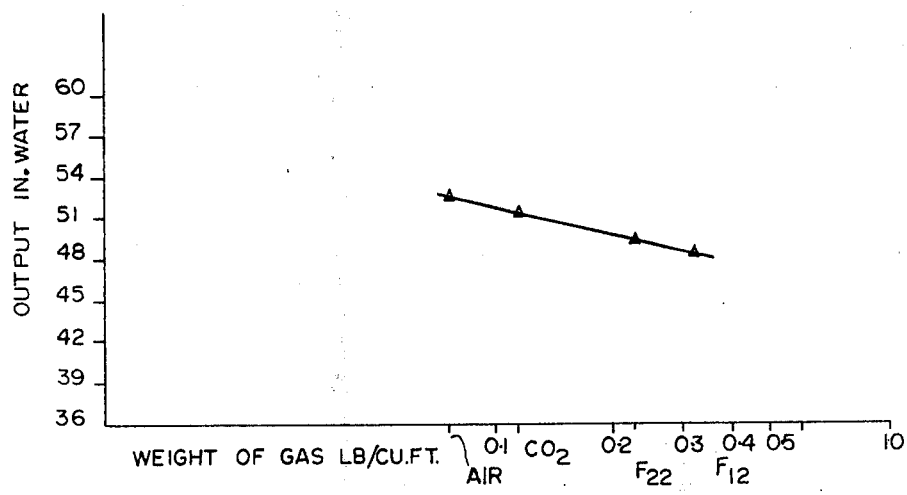
Figure 29:
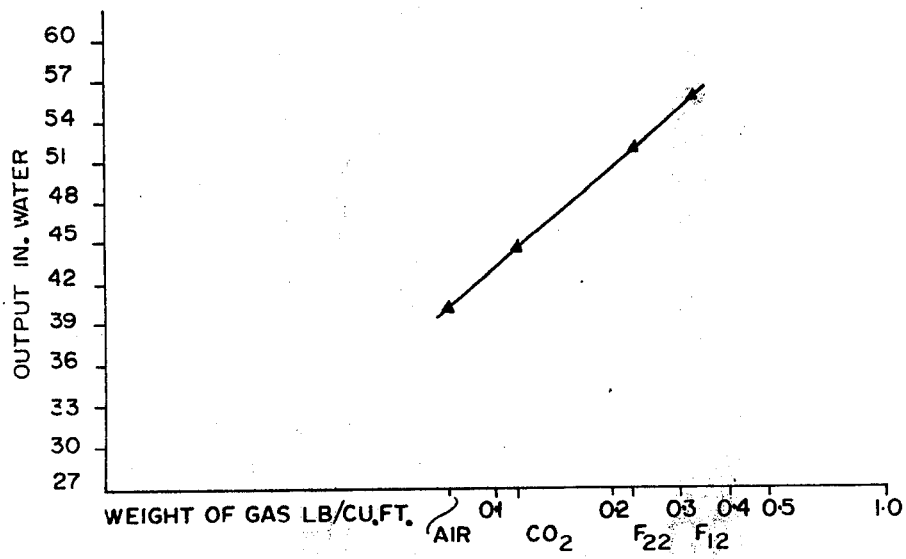

In the accompanying drawings which illustrate, by way of example, embodiments of the present invention:

FIG. 1 is a diagrammatic, partly sectioned corner view of an apparatus for measuring the velocity and/or density of a fluid stream, FIG. 2 is a graph of the axial velocity component of the fluid stream plotted against the receiver pressure for the apparatus shown in FIG. 1, FIG. 3 is a diagrammatic, partly sectioned side view of an apparatus for measuring the velocity of a fluid stream which has a different receiver means to the apparatus shown in FIG. 1, FIG. 4 is a diagrammatic, sectional side view of an apparatus for measuring the velocity of a fluid stream, having receiver means comprising two receiver tubes, FIG. 5 is a diagrammatic side view of an apparatus similar to the apparatus shown in FIG. 4 but with receiver means comprising four receiver tubes, FIG. 6 is a velocity diagram of the components of the fluid stream and the velocity measured by the apparatus shown in FIGS. 4 or 5, FIG. 7 is a diagram of the total head contours produced on the receiver means in FIGS. 4 or 5 by the velocity components shown in FIG. 6, FIG. 8 is a graph of the transverse velocity component of the fluid stream plotted against the receiver pressure for the apparatus shown in FIGS. 4 or 5, FIGS. 9 and 10 show different cap configurations that may be used with the apparatus shown in FIGS. 1, 3, 4 or 5, FIG. 11 is an apparatus similar to the apparatus shown in FIG. 4 but with a support for the receiver, FIG. 12 is a sectional end view along XII—XII, FIG. 11, FIGS. 13–15 are similar end views to FIG. 12 but of different receiver means, FIG. 16 is a side view of a similar apparatus to that shown in FIG. 5 but which is a conical configuration, FIG. 17 is a dome-shaped cap for use with the apparatus shown in FIG. 16, FIG. 18 is a similar apparatus to that shown in FIG. 5 but having a pyramidal configuration, FIG. 19 is an end view along XIX—XIX, FIG. 18, FIG. 20 is a side view of a similar apparatus to that shown in FIG. 18, but wherein the receiver means comprises two receiver tubes, FIG. 21 is a side view along XXI—XXI, FIG. 20, FIG. 22 is a side view of a similar apparatus to that shown in FIG. 5 but which is a hemispherical configuration, FIG. 23 is a side view of an apparatus similar to that shown in FIGS. 4 and 5 but which has tappings for measuring the static pressure, FIG. 24 is an apparatus similar to the apparatus shown in FIG. 23 but having a conical configuration, FIG. 25 is a sectional side view of a reference unit for use with any apparatus shown in FIGS. 1, 3, 4, 5, 9 to 24, FIG. 26 is a sectional side view of a different reference unit to that shown in FIG. 25 but for the same use, FIG. 27 is a sectional side view of yet another, different reference unit to that shown in FIG. 25 but for the same use, and FIGS. 28 and 29 are graphs of the density of a fluid plotted against the receiver pressure for the apparatus shown in FIG. 1.

Referring now to FIG. 1, there is shown an apparatus for measuring the velocity and/or density of a fluid stream comprising:

a. an elongated, fluid guiding member 1 which is symmetrical in cross-section about at least one plane A—A passing through a longitudinal axis B—B of the elongated, fluid guiding member 1, with the longitudinal axis B—B extending along a portion of the flow path of the fluid stream, b. nozzle means 2 for directing pressurized fluid along and in contact with at least, substantially identical opposing surface portions of the elongated, fluid guiding member 1 on each side of the plane A—A, c. means 4 for supplying the nozzle means 2 with the pressurized fluid, d. receiver means 6 having a receiver mouth 8, in the path of the fluid from the nozzle means 2, to have fluid pressure imposed in the receiver mouth 8 from the fluid directed along the opposing surfaces from the nozzle means 2, and e. indicating means 10 connected to the receiver means 6 for indicating, in terms of the fluid pressure in the receiver means 6, the velocity of the fluid stream, and wherein, f. the nozzle means 2 has a nozzle orifice 11 whose geometry is such that the Reynolds number at the nozzle orifice 11 is greater than 2,300 as defined in consistent units by:

$$Re = h\rho V/\mu$$

where
$Re$ = dimensionless Reynolds number,
$h$ = the mean height of the nozzle orifice 11 normal to the surface of the fluid guiding member 1,
$\rho$ = the density of the pressurized fluid supplied to the nozzle means 2, when the apparatus is in use,
$V$ = the mean velocity of the pressurized fluid in the nozzle orifice 11 when the apparatus is in use, and
$\mu$ = the viscosity of the pressurized fluid in the nozzle orifice 11 when the apparatus is in use.

Then used to measure the velocity of a fluid stream the apparatus shown in FIG. 1 measures only the principal component of the velocity of the fluid stream, that is the principal component flowing in the direction of the arrow X or the arrow Y.

The elongated, fluid guiding member 1 is a tube of circular cross-section having a circular bore 12 and so in this embodiment is symmetrical in cross-section about all planes extending through the longitudinal axis B—B.

The nozzle means 2 is a cap having a concavity 14 of circular cross-section and is coaxial with the guiding member 1.

The means 4 supplies pressurized air to the bore 12 by means of a connecting tube 16.

The receiver means 6 is a circular casing which is coaxial with and spaced from the elongated, fluid guiding member 1 and has an end wall 18 sealing the end of the receiver means 6 remote from the mouth 8 to the elongated, fluid guiding member 1.

The indicating means 10 is a manometer and is connected to the interior of the receiver means 6 to the pressurized by the fluid pressure in the receiver means 6.

In operation the apparatus was arranged as shown in FIG. 1, in a fluid stream whose velocity was to be measured, in this instance an air stream flowing at a velocity V ft/sec., in the direction of arrow X. The means 4 was caused to deliver pressurized air along the bore 12 of the elongated, fluid guiding member 1. The pressurized air passing along the bore 12 was directed by the nozzle orifice 11 along and in contact with the whole of the cylindrical, external surface of the elongated, fluid guiding member 1 to be guided therealong to the mouth 8 of the receiver means 6.

By having the geometry of the nozzle orifice 11 as defined above in relation to a Reynolds number at the nozzle orifice 11 greater than 2,300 the air was found to issue from the nozzle orifice 11 as a turbulent flow and so with no air stream flowing in the direction X the air from the nozzle orifice 11 of the nozzle means 2 mixed in a normal fashion with air therearound, and under these conditions the pressure in the receiver means 6 was found to be related only to the supply pressure and geometry of the apparatus.

The effect of a principal component of velocity, in the direction of arrow X, of an air stream flowing along and around the whole of the elongated, fluid guiding member 1 was found to be a reduction of the mixing of the air from the nozzle orifice 11 of the nozzle means 2 with the surrounding air and a reduction of the spreading angle of air from the nozzle means 2 (as depicted, for example, by the reduction from the dotted arrow lines, through the chain-dotted arrow lines to the solid arrow lines) and an increase in the pressure in the receiver means 6 then becomes a function of the air supply pressure to the nozzle means 2, the geometry of the nozzle orifice 11 of the nozzle means 2, and the magnitude of the principal component of velocity, in the direction arrow X, of the air stream. With the geometry of the nozzle orifice 11 as defined above to produce turbulent flow the magnitude of the principle component of velocity in the direction of arrow X was found to be related to the pressure in the receiver means 6 in a consistent manner, in other words without this geometry of the nozzle orifice 11 the nozzle jet may not have turbulent flow and a different pressure in the receiver means 6 may be measured for the same magnitude of the principle component of velocity X in different tests. The same was found to apply when the principle component of velocity was in the direction of arrow Y.

In FIG. 2 the increase in the pressure in the receiver means 6, indicated in inches of water by the manometer 10, FIG. 1, is shown plotted against the principal component of velocity, in the direction of arrow X (FIG. 1), of the air stream. The stability of the flow of air along the elongated, fluid guiding member 1 is reflected in the straight line relationship.

In FIG. 3, where similar parts to those shown in FIG. 1 are designated by the same reference numerals and the previous description is relied upon to describe them, the receiver means 6 comprises two coaxial casings 20 and 22 and an end wall 24 sealing the annular space between 26 between the casings 20 and 22. The receiver mouth 8 leads to the space 26 while the annular space 28 bounded by casing 20 acts as a vent. This embodiment is particularly useful where the nozzle means 2 and the mouth 8 of the receiver means 6 are spaced some distance apart such as at least four times the maximum diameter of the concavity of the nozzle means 2.

The embodiment shown in FIG. 3 can be used in the same manner as the embodiment described, with reference to FIG. 1, to measure the velocity of a fluid stream.

Referring now to FIG. 4, where parts similar to those shown in FIG. 1 are designated by the same reference numerals and the previous description is relied upon to describe them, the receiver means comprises two receiver tubes 30 and 32 each connected to a different manometer (not shown) of the type designated 10, FIG. 1. The receiver tubes 30 and 32, are spaced 180° from one another around the elongated, fluid guiding member 1 and are equally spaced from the longitudinal axis thereof. The fluid guiding member 1, being circular in cross-section, is symmetrical about a horizontal plane passing through the longitudinal axis and so presents substantially identical opposing surface portions to the flow from the nozzle means to each receiver tube 30 and 32.

The embodiment shown in FIG. 4 can be used in the same manner as the embodiment described with reference to FIG. 1 to measure the velocity of a fluid stream flowing in the direction of arrows X and Y (FIG. 1) but in this instance the velocity is derived from the sum of the fluid pressures in the receiver tubes 30 and 32.

In FIG. 5, where again the parts similar to those shown in FIG. 1 are designated by the same reference numerals and the previous description is relied upon to describe them, the receiver means comprises four receiver tubes 36 to 39 each connected to a different manometer (not shown) of the type shown and designated 10, FIG. 1. The four receiver tubes 36 to 39 are equally spaced around the elongated, fluid guiding member 1, and are equally spaced from the longitudinal axis thereof.

For measuring the velocity of a fluid stream flowing in the direction of X or Y (FIG. 1) the apparatus of FIG. 5 is used in the same manner as the apparatus described with reference to FIG. 4, that is, the velocity of the fluid stream is derived from the sum of the fluid pressures in the receiver tubes 36 to 39.

Referring now to FIG. 6 when the apparatus shown in either of FIGS. 4 or 5 is used to measure only the principal component (X or Y) of velocity of an air stream shown in the velocity diagram, the initial pressure in each receiver tube is measured with air impinging thereon from the nozzle means 2 but with no fluid stream flowing over the apparatus. The final pressure in each receiver tube is then measured with air impinging thereon from the nozzle means 2 and with the fluid stream flowing over the apparatus. The sum of the initial pressures is then subtracted from the sum of the final pressures and the resulting pressure compared with previous readings to obtain the principal velocity of the fluid stream.

When, however, the apparatus shown in either of FIGS. 4 or 5 is used to measure the principal component (X or Y) and secondary component Z of velocity M shown in the velocity diagram the principal component is deduced as described above. The effect of the secondary component Z is to move the total head contours from a position where they are coaxial with the total head contours have been pushed off-center by the momentum in the direction of the secondary component Z of fluid from the fluid stream which has become entrained in fluid from the nozzle means 2. Such as the off-center position shown in FIG. 7. It will be appreciated that the total head contours in FIG. 7 depict a relatively high pressure at dashed circle 40, an intermediate pressure at dashed circle 42 and a relatively low pressure at dashed circle 44. The effect of the static pressure gradients caused by the secondary component Z will also have an effect on the fluid from the nozzle means and will contribute to decreased spreading thereof on the upstream side of the elongated fluid guiding member 1 to the secondary component and increased spreading on the downstream side.

Thus with one of the receiver tubes of either of the embodiments shown in FIGS. 4 and 5 lying directly upstream, of the elongated, fluid guiding member, to the secondary component Z and another lying directly downstream thereof, a greater total head pressure is imposed on the receiver tube lying upstream of the secondary component Z than that on the receiver tube lying downstream thereof. The secondary component Z can be obtained by subtracting the final pressure of the upstream receiver from the final pressure of the downstream receiver and deducing from previous results the velocity of the secondary component Z of the fluid stream.

The other two receivers in the embodiment shown in FIG. 5 can be used to calculate whether a velocity component exists which is at right angles to the secondary component Z and transverse to the longitudinal axis of the fluid guiding member 1.

FIG. 8 is a graph showing the differential output pressure of the receivers of FIGS. 4 and 5 for the secondary component Z, plotted against the velocity of the secondary component Z.

It will be appreciated that the apparatus shown in FIGS. 4 and 5 can also be used to measure the velocity of a fluid stream whose major or sole component of velocity is in the direction of arrow Z.

Figure 9:
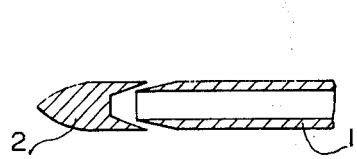

Referring now to FIGS. 9 and 10, where parts similar to those shown in FIG. 1 are designated by the same reference numeral and the previous description is relied upon to describe them, the nozzle means 2 may have a maximum diameter equal to the maximum diameter of the elongated, fluid guiding member 1, as shown in FIG. 9, or may have a maximum diameter smaller than the maximum diameter of the elongated, fluid guiding member 1, as shown in FIG. 10. The use of a smaller nozzle means as shown in FIG. 10 will require contouring the end 46 of the elongated, fluid guiding member 1 to ensure that fluid issuing from the nozzle means 2 will flow attached to the surface of the elongated, fluid guiding member 1 by means of the well known "Coanda" effect.

In FIGS. 11 and 12, parts similar to those shown in FIG. 5 are designated by the same reference numerals and the previous description is relied upon to describe them. The receiver tubes 36 to 39 are secured to a support tube 48.

Figure 13:
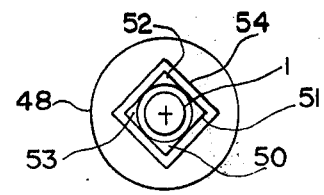

FIGS. 13 to 15 show different receiver tube arrangements for use with the apparatus shown in FIGS. 11 and 12. In FIG. 13 the interstices 50 to 53 between the elongated, fluid guiding member 1, and a close fitting tube 54 of square cross-section, form the receiver tubes. In FIG. 14 the receiver tubes are provided by four U-shaped conduits 56 to 59 sealed to the elongated, fluid guiding member 1. In FIG. 15 tubes 60 to 63 of rectangular cross-section are used for the receiver tubes.

The cross-sectional shape of the receiver tubes affects the characteristics of the apparatus and the receivers are preferably chosen to produce specified output characteristics within the limits of the phenomena involved in the fluid stream to be measured.

FIG. 16 shows an apparatus similar to that shown in FIG. 5 with four receiver tubes, but of conical form. The elongated, fluid guiding member 64 is cone shaped and circular in cross-section. The nozzle means 66 has a similar shaped concavity to the nozzle means 2 of FIG. 1. Four receiver tubes 67 to 70 are equally spaced around, and from the longitudinal axis of, the elongated, fluid guiding member 64. The receiver tubes 67 to 70 each extend parallel to the portion of the surface of the elongated, fluid guiding member 64 to which they are adjacent. This embodiment reduces the possibility of the fluid from the nozzle means 66 separating from the surface of the elongated, fluid guiding member 64, through the momentum of fluid issuing from the nozzle means 66.

FIG. 17 shows a different nozzle means 72 for use with the apparatus shown in FIG. 16. The end 74 of the elongated, fluid guiding member 64 is chamfered to fit into the nozzle means 72 with an annular space between these members.

In FIGS. 18 and 19 a pyramidal configuration is used. An elongated, fluid guiding member 76 is pyramidal in shape and of square cross-section with four receiver tubes 77 to 80. A nozzle means 82 is pyramidal in shape.

A wedge-shaped configuration is shown in FIGS. 20 and 21 using two receiver tubes 82 and 84 in the same manner as the embodiment shown in FIG. 4. In this embodiment the elongated, fluid guiding member 86 is wedge-shaped and has two flaps 88 and 90 cut therefrom and bent outwardly to form the nozzle means.

FIG. 22 shows a hemispherical configuration having four receiver tubes similar to the embodiment shown in FIG. 5. The elongated, fluid guiding member 92 has a hemispherically shaped end 94 with an outlet facing nozzle means 96. Four receiver tubes 97 to 100 are equally spaced around the elongated, fluid guiding member 92 and are shaped in a longitudinal direction to follow its contour and curve inwardly a little.

Particular applications may require the measurement of both total head and static pressure and FIG. 23 shows a modification of the apparatus shown in FIG. 4 for this purpose. The elongated, fluid guiding member 1 has two static pressure holes 102 and 104, and partitions 106 and 108, provide receiver chambers for measuring pressure changes at the static pressure holes 102 and 104 respectively by means of pressure measuring devices (not shown).

FIG. 24 shows a conical configuration, similar to that in FIG. 16 but having the static pressure holes 110 and 112 and partitions 114 and 116. The end cap 66 may be provided with an opening 118 in its apex for measuring the total head.

FIGS. 25 and 26 each show comparators to balance any biased output from any of the apparatus shown in FIGS. 1, 3, 4, 5, 9 to 22. A supply of fluid at the same velocity and pressure to that to the nozzle means is delivered to a nozzle 120 and the pressure in a receiver tube 122 is compared with that in the receiver means, whilst both apparatus are disposed in the fluid stream to be measured, to balance any biased output therefrom. In FIG. 25 the nozzle 120 and receiver tube 122 are mounted in a casing 124 having a vent 126 to expose the nozzle 120 and receiver tube 122 to the fluid stream. In FIG. 26 the nozzle 120 and receiver tube 122 are mounted in a casing 128 having two vents 130 and 132 for exposing the nozzle 120 and receiver tube 122 to the fluid stream.

In FIG. 27 a comparator is shown which is similar in construction to the apparatus shown in FIG. 4 in that an elongated, fluid guiding member 134 has two receiver tubes 136 and 138, and leads to a nozzle means 140. The elongated, fluid guiding member 134, receiver tubes 136 and 138 and nozzle means 140 are all mounted in a casing 142 having a vent 144. The comparator shown in FIG. 27 may be used in the same manner as the comparators shown in FIGS. 25 and 26.

The apparatus shown in FIGS. 1, 3, 4, 5 and 9 to 24 can also be used to measure the density of a stationary fluid induced to flow as a fluid stream by a jet from the nozzle or the density of a fluid stream flowing as previously described relative to these apparatus. Furthermore, the comparators shown in FIGS. 25 and 26 and 27 may also be used in the manner previously described but in conjunction with the apparatus shown in FIGS. 1, 3, 4, 5 and 9 to 24 to measure the density of a fluid.

In FIG. 28, wherein the apparatus shown in FIG. 1 is arranged in the same manner as previously described except that the spacing between the nozzle orifice and receiver mouth is 0.475 inches and the supply of pressurized air is such that a pressure of 15 pounds per square inch is maintained within the concavity 14, the relationship between the density of the gas surrounding the apparatus and the pressure in the receiver means is illustrated.

In FIG. 29, wherein the apparatus shown in FIG. 1 is arranged in the same manner as previously described except that the spacing between the nozzle orifice and the receiver mouth is 0.600 inches, the apparatus is surrounded by air and the supply of pressurized fluid consists of various gases such as air, carbon dioxide and freons, the relationship between the density of the fluid from the pressurized fluid source and the pressure in the receiver means is illustrated.

It will also be appreciated that the apparatus according to the present invention can be used to measure the density in addition to the velocity of a fluid stream.

The effect of the velocity of the fluid stream on the measurement of the density of the fluid when only the density is to be measured may be reduced by surrounding the apparatus with a shield or protective cover which may be porous or have provision for the entry and exit of the fluid whose density is to be measured.

I claim:

1. Apparatus for measuring the velocity and/or density of a fluid stream comprising:
   a. an elongated, fluid guiding member which is symmetrical in cross-section about at least one plane passing through and along a longitudinal axis of the elongated, fluid guiding member, with said longitudinal axis extending along a portion of the flow path of said fluid stream,
   b. nozzle means spaced from said member to define at least one nozzle orifice therewith and for directing pressurized fluid in the direction of said longitudinal axis and along and in contact with at least, substantially identical opposing surface portions of said member on each side of said plane,
   c. means for supplying said nozzle means with said pressurized fluid,
   d. receiver means alongside the said substantially identical opposing surface portions and having at least one receiver mouth, in the path of said pressurized fluid from said nozzle means, to have fluid pressure imposed therein from said fluid directed along said opposing surface portions from said nozzle means, and
   e. indicating means connected to said receiver means for indicating, in terms of the fluid pressure therein, the velocity and/or density of said fluid stream, and wherein
   f. the nozzle means has a nozzle orifice where geometry is such that the Reynolds number at the nozzle orifice is greater than 2,300 as defined in consistent units by:

$$Re = h\rho V/\mu$$

where
   $Re$ = dimensionless Reynolds number
   $h$ = the mean height of the nozzle orifice normal to the surface of the fluid guiding number
   $\rho$ = the density of the pressurized fluid supplied to the nozzle means when the apparatus is in use,
   $V$ = the mean velocity of the pressurized fluid in the nozzle orifice when the apparatus is in use, and
   $\mu$ = the viscosity of the pressurized fluid in the nozzle orifice when the apparatus is in use.

2. Apparatus according to claim 1, wherein said elongated, fluid guiding member is circular in cross-section.

3. Apparatus according to claim 2, wherein said nozzle means directs fluid along, and around the whole of the circular cross-section of said elongated, fluid guiding member, and said receiver means has a receiver mouth which is pressurized by fluid around the whole of said elongated, fluid guiding member.

4. Apparatus according to claim 2, wherein said nozzle means directs fluid along, and around the whole of the circular cross-section of, said elongated, fluid guiding member, and said receiver means has two receiver mouths on diametrically opposite sides of said elongated, fluid guiding member, and aligned with said opposing surface portions.

5. Apparatus according to claim 1, wherein said elongated, fluid guiding member has a fluid passage extending therealong to an open end thereof remote from said receiver means, said nozzle means is a hollow cap over said open end and is for redirecting fluid, flowing along said fluid passage, in the direction of said longitudinal axis and toward and along said opposing surface portions, said receiver means is alongside said elongated, fluid guiding member for receiving pressurized fluid or a portion thereof in an annulus which is substantially concentric with the said longitudinal axis, and said means for supplying said nozzle with pressurized fluid is connected to said elongated, fluid guiding member to supply pressurized fluid along said fluid passage towards the open end thereof.

* * * * *